United States Patent
Burdette et al.

(10) Patent No.: US 11,827,553 B2
(45) Date of Patent: Nov. 28, 2023

(54) METHOD FOR CONTROLLING COMPACTION

(71) Applicant: CORNING INCORPORATED, Corning, NY (US)

(72) Inventors: Steven Roy Burdette, Big Flats, NY (US); Shriram Palanthandalam Madapusi, Painted Post, NY (US); Jeremy Nathan Payne, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 204 days.

(21) Appl. No.: 16/619,304

(22) PCT Filed: Jun. 14, 2018

(86) PCT No.: PCT/US2018/037596
§ 371 (c)(1),
(2) Date: Dec. 4, 2019

(87) PCT Pub. No.: WO2018/232153
PCT Pub. Date: Dec. 20, 2018

(65) Prior Publication Data
US 2020/0095155 A1      Mar. 26, 2020

Related U.S. Application Data

(60) Provisional application No. 62/519,347, filed on Jun. 14, 2017.

(51) Int. Cl.
*C03B 17/06* (2006.01)
*C03B 25/02* (2006.01)
*G01N 33/38* (2006.01)

(52) U.S. Cl.
CPC .......... *C03B 17/067* (2013.01); *C03B 25/025* (2013.01); *G01N 33/386* (2013.01)

(58) Field of Classification Search
None
See application file for complete search history.

(56) References Cited

U.S. PATENT DOCUMENTS 5,694,479 A * 12/1997 Guering ............... G01N 21/958
356/392
5,882,371 A     3/1999 Miyazaki et al.
(Continued)

FOREIGN PATENT DOCUMENTS

CN    1149283 A    5/1997
CN    101774751 A   7/2010
(Continued)

OTHER PUBLICATIONS

Walter M. Buehl et al. Thermal Compaction Modeling of Corning Code 7059 Fusion Drawn glass (Year: 1991).*
(Continued)

*Primary Examiner* — Jodi C Franklin
(74) *Attorney, Agent, or Firm* — Kevin M. Able

(57) ABSTRACT

A method of controlling compaction including obtaining a plurality of sets of process conditions for a plurality of glass ribbons, measuring a compaction value for a glass sheet cut from each glass ribbon of the plurality of glass ribbons, correlating the compaction to the process conditions. The method further includes selecting a predetermined cooling curve including a plurality of cooling rates, modifying the cooling curve by varying cooling rates of the plurality of cooling rates, calculating a predicted compaction value for a glass sheet cut from a glass ribbon drawn using the modified cooling curve, and repeating the modification and predicting until compaction is minimized.

4 Claims, 5 Drawing Sheets

(56) References Cited

U.S. PATENT DOCUMENTS

| | | | |
|---|---|---|---|
| 6,374,640 B1* | 4/2002 | Fotheringham | C03B 32/00 65/111 |
| 7,207,193 B2 | 4/2007 | Xun et al. | |
| 8,136,371 B2 | 3/2012 | Kato et al. | |
| 8,429,936 B2 | 4/2013 | Allan et al. | |
| 8,666,705 B2 | 3/2014 | Allan et al. | |
| 8,857,215 B2 | 10/2014 | Dale et al. | |
| 9,051,206 B2 | 6/2015 | Allan et al. | |
| 9,328,013 B2* | 5/2016 | Allan | C03C 3/087 |
| 9,533,907 B1* | 1/2017 | Allan | C03B 5/24 |
| 9,573,839 B2 | 2/2017 | Allan et al. | |
| 10,216,871 B2* | 2/2019 | Allan | G06F 30/20 |
| 10,846,446 B2* | 11/2020 | Allan | C03B 1/00 |
| 11,023,630 B1* | 6/2021 | Allan | G06F 17/11 |
| 2004/0055338 A1* | 3/2004 | Helfinstine | C04B 35/481 65/374.13 |
| 2005/0096777 A1* | 5/2005 | Allan | G05B 13/024 700/157 |
| 2007/0066734 A1* | 3/2007 | Ding | C08G 73/10 524/404 |
| 2007/0130994 A1* | 6/2007 | Boratav | C03B 17/064 65/29.21 |
| 2007/0190340 A1* | 8/2007 | Coppola | C03C 17/02 428/432 |
| 2007/0191207 A1* | 8/2007 | Danielson | C03C 3/095 501/72 |
| 2007/0220920 A1* | 9/2007 | Allaire | C03B 25/12 65/29.12 |
| 2008/0139377 A1* | 6/2008 | Helfinstine | C04B 35/49 501/106 |
| 2009/0100873 A1* | 4/2009 | Allan | C03B 17/067 65/85 |
| 2009/0131241 A1* | 5/2009 | Godard | C04B 35/447 501/106 |
| 2010/0126221 A1* | 5/2010 | Danielson | C03B 32/00 65/95 |
| 2011/0045961 A1* | 2/2011 | Dejneka | C03C 21/00 501/66 |
| 2011/0265516 A1* | 11/2011 | Allan | C03B 25/025 65/29.19 |
| 2012/0083915 A1* | 4/2012 | Allan | G01N 11/00 700/104 |
| 2013/0086952 A1* | 4/2013 | Charbonneau | C03B 5/24 65/29.13 |
| 2013/0133370 A1* | 5/2013 | Boratav | C03B 17/064 65/84 |
| 2013/0225390 A1* | 8/2013 | Ellison | C03C 3/093 501/66 |
| 2013/0292863 A1* | 11/2013 | Shoemake | B29C 67/249 366/76.2 |
| 2014/0013805 A1* | 1/2014 | Kariya | C03B 17/067 65/85 |
| 2014/0033768 A1* | 2/2014 | Isono | C03B 11/122 65/90 |
| 2014/0124965 A1* | 5/2014 | Takemura | B29C 59/02 264/1.24 |
| 2014/0179510 A1* | 6/2014 | Allan | C03C 3/091 501/67 |
| 2015/0099110 A1* | 4/2015 | Bellman | H01L 51/0097 156/308.2 |
| 2015/0306282 A1* | 10/2015 | Scanlon | A61L 31/18 623/1.34 |
| 2015/0343678 A1* | 12/2015 | Takemura | B29C 59/026 425/193 |
| 2016/0256116 A1* | 9/2016 | Baik | A61B 5/0059 |
| 2017/0076024 A1* | 3/2017 | Allan | C03B 1/00 |
| 2017/0082577 A1* | 3/2017 | Roussev | C03C 21/002 |
| 2017/0144918 A1 | 5/2017 | Allan et al. | |
| 2019/0147126 A1* | 5/2019 | Allan | C03B 1/00 65/29.11 |
| 2021/0292212 A1* | 9/2021 | Chen | C03B 17/064 |

FOREIGN PATENT DOCUMENTS

| | | |
|---|---|---|
| CN | 101925546 A | 12/2010 |
| CN | 102173565 A | 9/2011 |
| CN | 102173566 A | 9/2011 |
| CN | 202988955 U | 6/2013 |
| CN | 103732771 A | 4/2014 |
| CN | 105973927 A | 9/2016 |
| JP | 2009-502706 A | 1/2009 |
| JP | 2011-020864 A | 2/2011 |
| JP | 2012-076974 A | 4/2012 |
| TW | 201527231 A | 7/2015 |
| WO | 2005/055284 A2 | 6/2005 |
| WO | 2012/158860 A1 | 11/2012 |
| WO | 2016/052426 A1 | 4/2016 |

OTHER PUBLICATIONS

Annealing Glass by cyclic shear Deformation, The Journal of Chemical physics Das et al. (Year: 2022).*

Annealing glass by cyclic shear deformation, The Journal of Chemical Phys Das et al. (Year: 2022).*

Taiwanese Patent Application No. 107120321, Office Action dated Aug. 9, 2021, 3 page (English Translation Only); Taiwanese Patent Office.

International Search Report and Written Opinion of the International Searching Authority; PCT/US2018/037596; dated Feb. 15, 2019; 10 Pages; Korean Intellectual Property Office.

Chinese Patent Application No. 201880040183.6, Office Action dated Nov. 30, 2021, 12 pages (5 pages of English Translation and 7 pages of Original Document), Chinese Patent Office.

He et al., "Compaction of Glass Substrates for Active-matrix Liquid Crystal Display", Materials Reports, No. 6, 1999, 3 pages.

Japanese Patent Application No. 2019-568339, Office Action dated Jan. 12, 2022, 4 pages (2 pages of English Translation and 2 pages of Original Document), Japanese Patent Office.

Liu, "Application of Regression Analysis in Glass", China Glass, No. 4, 2002, 7 pages. (1 page of English translation and 6 pages of Original document.).

* cited by examiner

METHOD FOR CONTROLLING COMPACTION

CROSS-REFERENCE TO RELATED APPLICATIONS

The application claims the benefit of priority under 35 U.S.C. § 371 of International Application No. PCT/US18/37596, filed on Jun. 14, 2018, which claims the benefit of priority of U.S. Provisional Application Ser. No. 62/519,347 filed on Jun. 14, 2017 the contents of which are relied upon and incorporated herein by reference in their entirety as if fully set forth below.

BACKGROUND

Field

The present disclosure relates generally to methods for reducing distortion of glass substrates, and more particularly, to minimizing compaction thereof.

Technical Background

Glass display panels in the form of liquid crystal displays (LCDs) are used in an increasing variety of applications—from hand-held phones to computer monitors to television displays. These applications require glass sheets with pristine, defect-free surfaces. LCDs are comprised of thin sheets of glass sealed together to form an envelope. It is highly desirable that the dimensions of glass sheets comprising these displays do not vary when thermally cycled to maintain proper registration, or alignment, between elements comprising the LCD.

Typically, LCDs are of the amorphous silicon (a-Si) thin film transistor (TFT) or polycrystalline-silicon (ρ-Si or poly-Si) TFT type. Poly-Si has a much higher drive current and electron mobility, thereby decreasing the response time of the pixels. Further, it is possible, using ρ-Si processing, to build the display drive circuitry directly on the glass substrate. By contrast, α-Si requires discrete driver chips that must be attached to the display periphery utilizing integrated circuit packaging techniques.

However, the manufacture of ρ-Si TFTs requires higher processing temperatures than α-Si TFTs, thereby increasing the risk of glass shrinkage (compaction) during processing. In addition, continuing improvements in display resolution by increasing pixel density has also required commensurate improvements in glass thermal stability to ensure proper alignment of display components during manufacture, such as during deposition of thin film transistors on the glass substrate.

Glass manufacturers have often subjected glass substrates to a heat treatment prior to shipping the glass substrates to customers so that the substrates do not shrink, or shrink very little, when subjected to later thermal cycling in a customer process. Such heat treatments are known as "pre-shrinking" or "pre-compacting." High temperature processing, such as required by ρ-Si TFTs, may require long heat treatment times for the glass substrate to ensure low compaction, e.g., 5 hours at 600° C. Moreover, such heat treatments involve further handling of the glass substrates, increasing the chances of damage to the surfaces of the substrates as well as increasing overall manufacturing costs.

Quantitatively, compaction is the change in length per unit length exhibited by a glass substrate in a plane of the substrate as a result of subtle changes in glass structure produced by thermal cycling (i.e., compaction is strain resulting from the thermal history of the glass and is closely associated with the fictive temperature of the glass). Compaction can be determined physically by placing marks on a glass substrate and measuring the initial distance between the marks. The substrate is then subjected to a predetermined heat treatment and returned to room temperature. The distance between the marks is then re-measured. Compaction in parts-per-million (ppm) is then given by: compaction=$10^6$ · (distance before heat treatment—distance after heat treatment)/(distance before heat treatment).

Because compaction is of concern to LCD panel manufacturers, in the past, as molten glass flow increases were made to increase output, the manufacturing process was linearly scaled to allow sufficient time during cooling to maintain the same compaction of the finished substrates as existed before the flow increase. Although this approach works to an extent, it has the drawback that it can require an increased distance between the forming body and the location where substrates are separated from the glass ribbon. These longer distances take up additional manufacturing space and capital to implement. Indeed, due to the physical constraints of existing facilities, increasing the draw distance to reduce compaction can limit the maximum flow available to a given glass forming installation. Moreover, ensuring the appropriate compaction often required significant experimentation to obtain the appropriate process conditions. It would be beneficial to be able to predict the compaction obtained by selected process conditions.

SUMMARY

In accordance with an embodiment of the present disclosure, a method of controlling compaction is disclosed, comprising:
a) measuring compaction for a plurality of glass sheets cut from a plurality of glass ribbons formed with different cooling rates;
b) correlating the measured compaction with the cooling rates of step a) to obtain a plurality of regression coefficients corresponding to a plurality of temperatures; c) selecting a predetermined cooling curve, the predetermined cooling curve comprising a plurality of predetermined cooling rates at the corresponding plurality of temperatures of step (b);
d) using the plurality of regression coefficients and the plurality of predetermined cooling rates to calculate a predicted compaction resulting from the predetermined cooling curve;
e) modifying the predetermined cooling rates to minimize the predicted compaction and obtain target cooling rates;
f) drawing a subsequent glass ribbon using the target cooling rates.

The method may further comprise substituting the modified cooling rates of step e) for the predetermined cooling rates of step d), and repeating steps d) and e) to obtain new target cooling rates prior to step f). This iterative process may be repeated as many times as necessary until a target cooling rate is obtain that minimizes compaction.

Step b) may comprise a linear regression, such as of the form $$\begin{bmatrix} k \\ \vdots \\ k \end{bmatrix} + \begin{bmatrix} q_1^1 & \cdots & q_1^n \\ \vdots & \ddots & \vdots \\ q_i^1 & \cdots & q_i^n \end{bmatrix} \times \begin{bmatrix} b_1 \\ \vdots \\ b_n \end{bmatrix} = \begin{bmatrix} C_1 \\ \vdots \\ C_i \end{bmatrix},$$

where q represents cooling rate in °C./second, b represents the regression coefficients, C represents compaction in parts per million, i represents a total number of data sets, n represents a total number of the regression coefficients, and k represents an intercept of the regression.

The predicted compaction value can be calculated from the equation, $$\text{Compaction} = k + \Sigma_{n=1}^{n=m}(b_n \times q_n), \text{ where}$$

k is an intercept of the regression, m represents a number of temperature increments over a temperature range from x° C. to y° C., n represents a number of temperature increments, b represents the regression coefficients and q represents cooling rate.

In some embodiments, x is equal to 450° C. and y is equal to 900° C.

In another embodiment, a method of controlling compaction is described, comprising:
a) drawing a glass ribbon from a forming body at a first draw rate;
b) measuring temperature along a centerline of the glass ribbon at a plurality of distances from a bottom edge of the forming body;
c) calculating cooling rates for the glass ribbon at the plurality of distances based on the measured temperatures;
d) measuring compaction of a glass sheet cut from the glass ribbon;
e) repeating steps a) through d) for a plurality of glass ribbons drawn at a plurality of draw rates to obtain a plurality of measured compaction values;
f) correlating the plurality of measured compaction values with the cooling rates at the plurality of distances for the plurality of glass ribbons to obtain a plurality of regression coefficients corresponding to a plurality of temperatures in a predetermined temperature range;
g) selecting a predetermined cooling curve, the predetermined cooling curve comprising a predetermined cooling rate at each corresponding temperature of the plurality of temperatures;
h) using the plurality of regression coefficients and the plurality of predetermined cooling rates to obtain a predicted compaction value at a predetermined draw rate;
i) modifying the predetermined cooling rates to minimize the predicted compaction value at the predetermined draw rate and obtain target cooling rates;
j) drawing a subsequent glass ribbon using the target cooling rates.

The method may further comprise substituting the modified cooling rates of step i) for the predetermined cooling rates of step h), and repeating steps h) and i) to obtain new target cooling rates prior to step j). This iterative process may be repeated as many times as necessary until a target cooling rate is obtain that minimizes compaction.

Step f) may comprise, a linear regression, such as a system of linear equations of the form $$\begin{bmatrix} k \\ \vdots \\ k \end{bmatrix} + \begin{bmatrix} q_1^1 & \cdots & q_1^n \\ \vdots & \ddots & \vdots \\ q_i^1 & \cdots & q_i^n \end{bmatrix} \times \begin{bmatrix} b_1 \\ \vdots \\ b_n \end{bmatrix} = \begin{bmatrix} C_1 \\ \vdots \\ C_i \end{bmatrix},$$

where q represents cooling rate in °C./second, b represents the regression coefficients, C represents compaction value in parts per million, i represents a total number of data sets, n represents a total number of temperature increments, and k represents an intercept of the regression.

The predicted compaction value can be calculated as, $$\text{Compaction} = k + \Sigma_{n=1}^{n=m}(b_n \times q_n), \text{ where}$$

k is an intercept of the regression, m represents a number of temperature increments over a temperature range from x° C. to y° C., n represents temperature increments, b is a regression coefficient and q is cooling rate.

In some embodiments, x is equal to 450° C. and y is equal to 900° C.

Additional features and advantages of the embodiments disclosed herein will be set forth in the detailed description that follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments intended to provide an overview or framework for understanding the nature and character of the embodiments disclosed herein. The accompanying drawings are included to provide further understanding, and are incorporated into and constitute a part of this specification. The drawings illustrate various embodiments of the disclosure, and together with the description serve to explain the principles and operations thereof.

DETAILED DESCRIPTION

Figure 1:
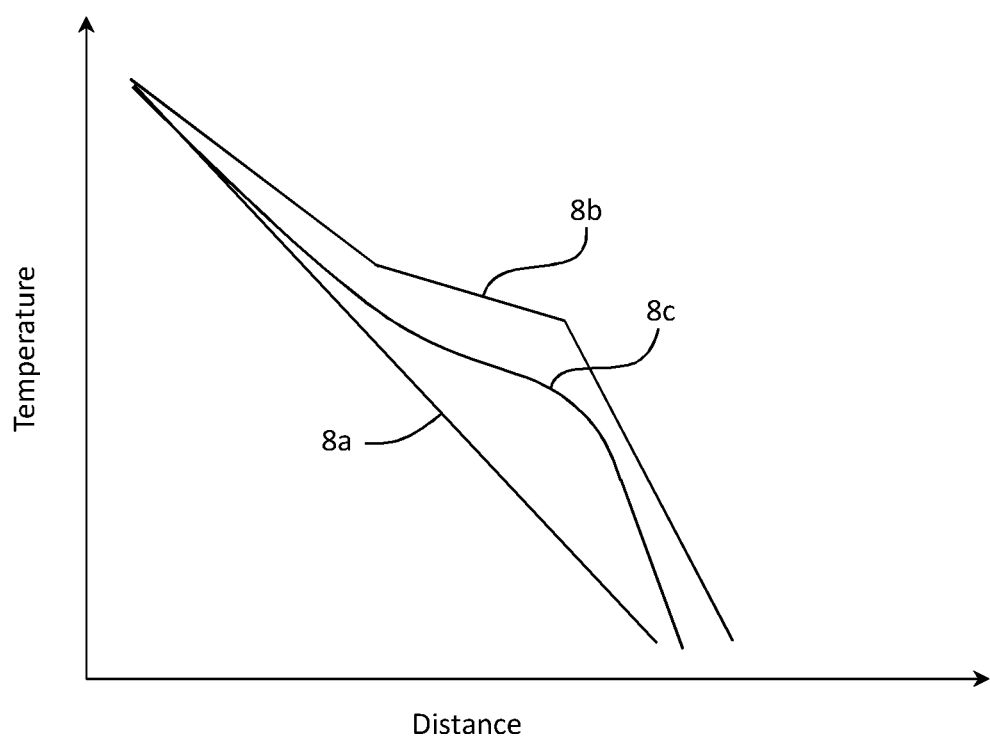
FIG. 1 is a plot graphically showing several variations of exemplary cooling curves.

Reference will now be made in detail to embodiments of the present disclosure, examples of which are illustrated in the accompanying drawings. Whenever possible, the same reference numerals will be used throughout the drawings to refer to the same or like parts. However, this disclosure may be embodied in many different forms and should not be construed as limited to the embodiments set forth herein.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Directional terms as used herein—for example up, down, right, left, front, back, top, bottom—are made only with reference to the figures as drawn and are not intended to imply absolute orientation.

Unless otherwise expressly stated, it is in no way intended that any method set forth herein be construed as requiring that its steps be performed in a specific order, nor that with any apparatus, specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural references unless the context clearly dictates otherwise. Thus, for example, reference to "a" component includes aspects having two or more such components, unless the context clearly indicates otherwise.

As used herein, "molten glass" shall be construed to mean a molten material which, upon cooling, can enter a glassy state. The term molten glass is used synonymously with the term "melt". The molten glass may form, for example, a majority silicate glass, although the present disclosure is not so limited.

As used herein, the term "cooling curve" shall denote temperature as a function of distance, or alternatively as a function of time. Typically, distance is denoted relative to a bottom edge of a forming body from which the ribbon of molten glass is drawn. It should be recognized that time is directly relatable to distance given a known draw speed. A cooling curve may comprise one or more linear (constant) cooling rates, one or more nonlinear cooling rates, or a combination of linear and nonlinear cooling rates. For example, FIG. 1 depicts an exemplary cooling curve $8a$ shown plotted as temperature as a function of distance below the forming body. Cooling curve $8a$ comprises a single, linear cooling rate, whereas cooling curve $8b$ depicts a plurality of linear cooling rates (segments). Curve $8c$ comprises a nonlinear cooling curve. Cooling rates are determined as the slope of a tangent to the curve, or segment, at the point (e.g., temperature) of interest. It should be understood that the cooling curves shown in FIG. 1 are merely exemplary and presented for illustration, not limitation.

The manufacture of glass sheets by a draw process, for example a down draw process such as a fusion down draw process, requires careful control of temperature. The impact of temperature can be most acute during the forming process, where a thin glass ribbon, in many cases less than a millimeter (mm) or less in thickness and in some instances in excess of 3 meters wide, is drawn from a forming body through free space supported principally by its edges. For example, a thickness of the glass ribbon at the centerline of the glass ribbon may be equal to or less than about 1 mm, such as equal to or less than about 0.7 mm, equal to or less than about 0.5 mm, equal to or less than about 0.3 mm and in some embodiments, equal to or less than about 0.1 mm.

Figure 2:
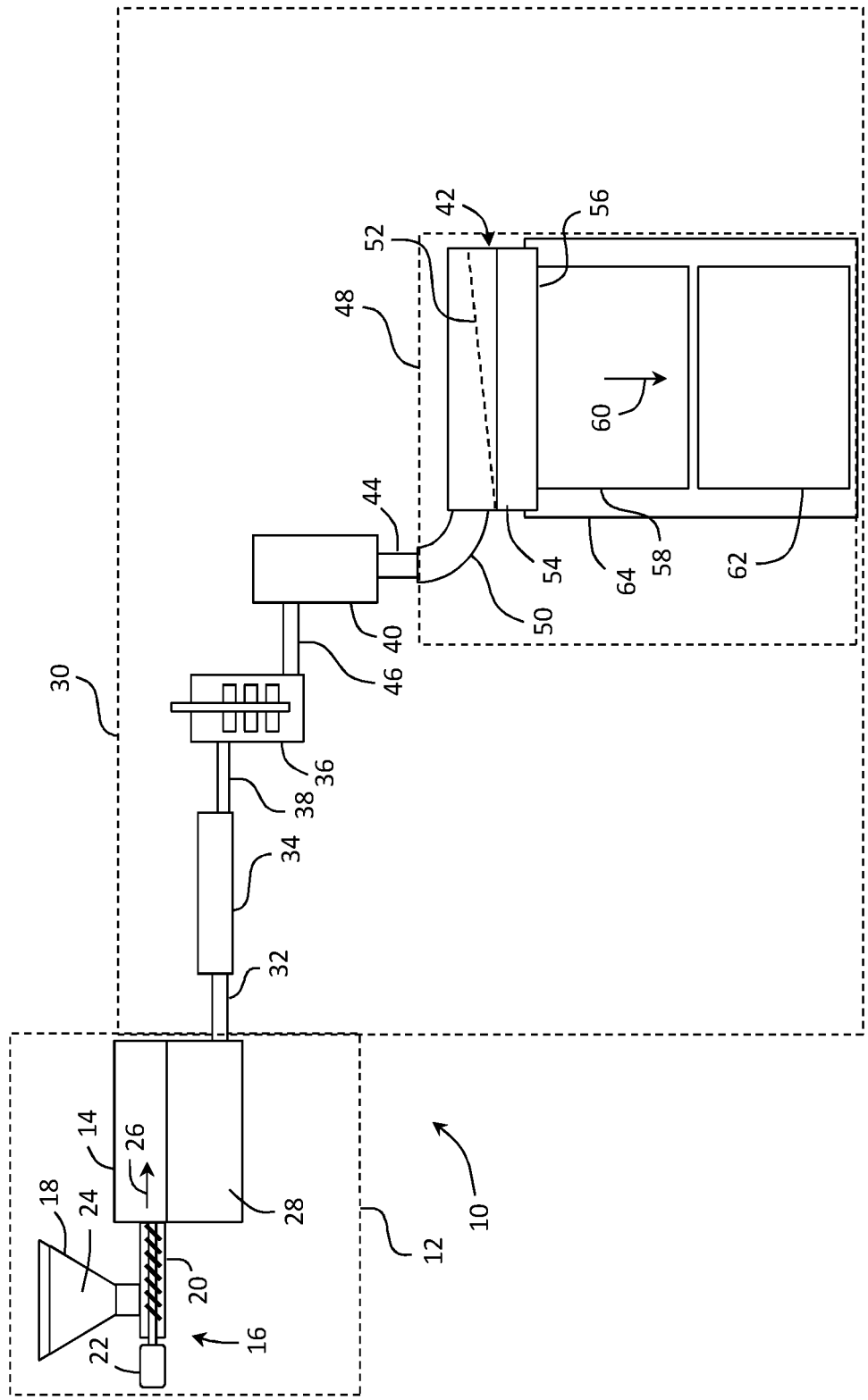
FIG. 2 is a schematic view of an exemplary fusion down draw apparatus.

By way of example, FIG. 2 illustrates an exemplary fusion glass manufacturing apparatus 10. In some embodiments, the glass manufacturing apparatus 10 can comprise a glass melting furnace 12 that can include a melting vessel 14. In addition to melting vessel 14, glass melting furnace 12 can optionally include one or more additional components such as heating elements (e.g., combustion burners and/or electrodes) configured to heat raw material and convert the raw material into molten glass. For example, melting furnace 14 may be an electrically-boosted melting vessel, wherein energy is added to the raw material through both combustion burners and by direct heating, wherein an electric current is passed through the raw material, and thereby adding energy via Joule heating of the raw material. As used herein, an electrically-boosted melting vessel is a melting vessel that obtains heat energy from both Joule heating and above-surface combustion heating, and the amount of energy imparted to the raw material and/or melt via Joule heating is equal to or greater than about 20%. As used herein, an electrically-boosted melting vessel does not include submerged combustion processes. In some embodiments, the heat energy added to the molten material by Joule heating (X) compared to the total heat energy added to the molten material via both above-surface combustion burners (Y) and Joule heating can be in a range from about 20% to about 80%. For example, the ratio X:Y of heat energy added to the molten material via Joule heating compared to above-surface combustion burners may be 20%:80%, 30%:70%, 40%:60%, 50%:50%, 60%:40%, 70%:30% or even 80%:20%, although in further embodiments other ratios may be used.

In further embodiments, glass melting furnace 12 may include thermal management devices (e.g., insulation components) that reduce heat loss from the melting vessel. In still further embodiments, glass melting furnace 12 may include electronic devices and/or electromechanical devices that facilitate melting of the raw material into a glass melt. Still further, glass melting furnace 12 may include support structures (e.g., support chassis, support member, etc.) or other components.

Glass melting vessel 14 is typically formed from a refractory material, such as a refractory ceramic material, for example a refractory ceramic material comprising alumina or zirconia, although the refractory ceramic material may comprise other refractory materials, such as yttrium (e.g., yttria, yttria stabilized zirconia, yttrium phosphate), zircon (ZrSiO4) or alumina-zirconia-silica or even chrome oxide, used either alternatively or in any combination. In some examples, glass melting vessel 14 may be constructed from refractory ceramic bricks.

In some embodiments, melting furnace 12 may be incorporated as a component of a glass manufacturing apparatus configured to fabricate a glass article, for example a glass ribbon of an indeterminate length, although in further embodiments, the glass manufacturing apparatus may be configured to form other glass articles without limitation, such as glass rods, glass tubes, glass envelopes (for example, glass envelopes for lighting devices, e.g., light bulbs) and glass lenses, although many other glass articles are contemplated. In some examples, the melting furnace may be incorporated as a component of a glass manufacturing apparatus comprising a slot draw apparatus, a float bath apparatus, a down draw apparatus (e.g., a fusion down draw apparatus), an up draw apparatus, a pressing apparatus, a rolling apparatus, a tube drawing apparatus or any other glass manufacturing apparatus that would benefit from the present disclosure. By way of example, FIG. 2 schematically illustrates glass melting furnace 12 as a component of a fusion down draw glass manufacturing apparatus 10 for fusion drawing a glass ribbon for subsequent processing into individual glass sheets or rolling the glass ribbon onto a spool.

Glass manufacturing apparatus 10 (e.g., fusion down draw apparatus 10) can optionally include an upstream glass manufacturing apparatus 16 positioned upstream relative to glass melting vessel 14. In some examples, a portion of, or the entire upstream glass manufacturing apparatus 16, may be incorporated as part of the glass melting furnace 12.

As shown in the embodiment illustrated in FIG. 2, the upstream glass manufacturing apparatus 16 can include a raw material storage bin 18, a raw material delivery device 20 and a motor 22 connected to the raw material delivery device. Storage bin 18 may be configured to store a quantity of raw material 24 that can be fed into melting vessel 14 of glass melting furnace 12 through one or more feed ports, as indicated by arrow 26. Raw material 24 typically comprises one or more glass forming metal oxides and one or more modifying agents. In some examples, raw material delivery device 20 can be powered by motor 22 such that raw material delivery device 20 delivers a predetermined amount of raw material 24 from the storage bin 18 to melting vessel 14. In further examples, motor 22 can power raw material delivery device 20 to introduce raw material 24 at a controlled rate based on a level of molten glass sensed downstream from melting vessel 14 relative to a flow direction of the molten glass. Raw material 24 within melting vessel 14 can thereafter be heated to form molten glass 28. Typically, in an initial melting step, raw material is added to the melting vessel as particulate, for example as comprising various "sands". Raw material may also include scrap glass (i.e. cullet) from previous melting and/or forming operations. Combustion burners are typically used to begin the melting process. In an electrically boosted melting process, once the electrical resistance of the raw material is sufficiently reduced (e.g., when the raw materials begin liquefying), electric boost is begun by developing an electric potential between electrodes positioned in contact with the raw materials, thereby establishing an electric current through the raw material, the raw material typically entering, or in, a molten state at this time.

Glass manufacturing apparatus 10 can also optionally include a downstream glass manufacturing apparatus 30 positioned downstream of glass melting furnace 12 relative to a flow direction of the molten glass 28. In some examples, a portion of downstream glass manufacturing apparatus 30 may be incorporated as part of glass melting furnace 12. However, in some instances, first connecting conduit 32 discussed below, or other portions of the downstream glass manufacturing apparatus 30, may be incorporated as part of the glass melting furnace 12. Elements of the downstream glass manufacturing apparatus, including first connecting conduit 32, may be formed from a precious metal. Suitable precious metals include platinum group metals selected from the group of metals consisting of platinum, iridium, rhodium, osmium, ruthenium and palladium, or alloys thereof. For example, downstream components of the glass manufacturing apparatus may be formed from a platinum-rhodium alloy including from about 70% to about 90% by weight platinum and about 10% to about 30% by weight rhodium. However, other suitable metals can include molybdenum, rhenium, tantalum, titanium, tungsten and alloys thereof.

Downstream glass manufacturing apparatus 30 can include a first conditioning (i.e. processing) vessel, such as fining vessel 34, located downstream from melting vessel 14 and coupled to melting vessel 14 by way of the above-referenced first connecting conduit 32. In some examples, molten glass 28 may be gravity fed from melting vessel 14 to fining vessel 34 by way of first connecting conduit 32. For instance, gravity may drive molten glass 28 through an interior pathway of first connecting conduit 32 from melting vessel 14 to fining vessel 34. It should be understood, however, that other conditioning vessels may be positioned downstream of melting vessel 14, for example between melting vessel 14 and fining vessel 34. In some embodiments, a conditioning vessel may be employed between the melting vessel and the fining vessel wherein molten glass from a primary melting vessel is further heated in a secondary vessel to continue the melting process, or cooled to a temperature lower than the temperature of the molten glass in the primary melting vessel before entering the fining vessel.

As described previously, bubbles may be removed from molten glass 28 by various techniques. For example, raw material 24 may include multivalent compounds (i.e. fining agents) such as tin oxide that, when heated, undergo a chemical reduction reaction and release oxygen. Other suitable fining agents include without limitation arsenic, antimony, iron and cerium, although as noted previously, the use of arsenic and antimony may be discouraged for environmental reasons in some applications. Fining vessel 34 is heated to a temperature greater than the melting vessel temperature, thereby heating the fining agent. Oxygen bubbles produced by the temperature-induced chemical reduction of one or more fining agents included in the melt rise through the molten glass within the fining vessel, wherein gases in the molten glass produced in the melting furnace can coalesce or diffuse into the oxygen bubbles produced by the fining agent. The enlarged gas bubbles with increased buoyancy can then rise to a free surface of the molten glass within the fining vessel and thereafter be vented out of the fining vessel. The oxygen bubbles can further induce mechanical mixing of the molten glass in the fining vessel as they rise through the molten glass.

The downstream glass manufacturing apparatus 30 can further include another conditioning vessel, such as a mixing apparatus 36, for example a stirring vessel, for mixing the molten glass that flows downstream from fining vessel 34. Mixing apparatus 36 can be used to provide a homogenous glass melt composition, thereby reducing chemical or thermal inhomogeneities that may otherwise exist within the fined molten glass exiting the fining vessel. As shown, fining vessel 34 may be coupled to mixing apparatus 36 by way of a second connecting conduit 38. In some embodiments, molten glass 28 may be gravity fed from the fining vessel 34 to mixing apparatus 36 by way of second connecting conduit 38. For instance, gravity may drive molten glass 28 through an interior pathway of second connecting conduit 38 from fining vessel 34 to mixing apparatus 36. Typically, the molten glass within the mixing apparatus includes a free surface, with a free volume extending between the free surface and a top of the mixing apparatus. It should be noted that while mixing apparatus 36 is shown downstream of fining vessel 34 relative to a flow direction of the molten glass, mixing apparatus 36 may be positioned upstream from fining vessel 34 in other embodiments. In some embodiments, downstream glass manufacturing apparatus 30 may include multiple mixing apparatus, for example a mixing apparatus upstream from fining vessel 34 and a mixing apparatus downstream from fining vessel 34. These multiple mixing apparatus may be of the same design, or they may be of a different design from one another. In some embodiments, one or more of the vessels and/or conduits may include static mixing vanes positioned therein to promote mixing and subsequent homogenization of the molten material.

Downstream glass manufacturing apparatus 30 can further include another conditioning vessel such as delivery vessel 40 that may be located downstream from mixing apparatus 36. Delivery vessel 40 may condition molten glass 28 to be fed into a downstream forming device. For instance, delivery vessel 40 can act as an accumulator and/or flow controller to adjust and provide a consistent flow of molten glass 28 to forming body 42 by way of exit conduit 44. The molten glass within delivery vessel 40 can, in some embodiments, include a free surface, wherein a free volume extends upward from the free surface to a top of the delivery vessel. As shown, mixing apparatus 36 may be coupled to delivery vessel 40 by way of third connecting conduit 46. In some examples, molten glass 28 may be gravity fed from mixing apparatus 36 to delivery vessel 40 by way of third connecting conduit 46. For instance, gravity may drive molten glass 28 through an interior pathway of third connecting conduit 46 from mixing apparatus 36 to delivery vessel 40.

Downstream glass manufacturing apparatus 30 can further include forming apparatus 48 comprising the above-referenced forming body 42, including inlet conduit 50. Exit conduit 44 can be positioned to deliver molten glass 28 from delivery vessel 40 to inlet conduit 50 of forming apparatus 48. Forming body 42 in a fusion down draw glass making apparatus can comprise a trough 52 positioned in an upper surface of the forming body and converging forming surfaces 54 (only one surface shown) that converge in a draw direction along a bottom edge (root) 56 of the forming body. Molten glass delivered to the forming body trough via delivery vessel 40, exit conduit 44 and inlet conduit 50 overflows the walls of the trough and descends along the converging forming surfaces 54 as separate flows of molten glass. It should be noted that the molten glass within the forming body trough comprises a free surface, and a free volume extends from the free surface of the molten glass to the top of an enclosure within which the forming body is positioned. The separate flows of molten glass join below and along the root to produce a single ribbon of molten glass 58 that is drawn in a draw direction 60 from root 56 by applying a downward tension to the glass ribbon, such as by gravity, edge rolls and pulling rolls (not shown), to control the dimensions of the glass ribbon as the molten glass cools and a viscosity of the material increases. Accordingly, glass ribbon 58 goes through a visco-elastic transition and acquires mechanical properties that give glass ribbon 58 stable dimensional characteristics. Glass ribbon 58 may in some embodiments be separated into individual glass sheets 62 by a glass separation apparatus (not shown) in an elastic region of the glass ribbon, while in further embodiments, the glass ribbon may be wound onto spools and stored for further processing.

It should be readily apparent that even small temperature variations along and across a glass ribbon drawn through free space can result in residual stress that can warp the glass ribbon, and the glass sheet cut therefrom. It is also important to note that the ribbon typically leaves the forming body at a temperature in excess of 1000° C., but must be cooled to a temperature less than only several hundred degrees in a very short distance since the ribbon is typically drawn in a vertical downward direction and available vertical distance is often limited by practical considerations.

It should be further recognized that the capital expenditure required to assemble and operate a down draw glass making process, particularly for the production of optical quality glass, can be quite large. For example, with the exception of melting vessel 14 and forming vessel 42, which are usually constructed from a non-metallic refractory material, the remainder of the apparatus, including intervening vessels and conduits that carry the molten glass from the melting vessel to the forming body, are formed from one or more precious metals. Accordingly, changes in production volume demand beyond the existing apparatus limits are difficult and expensive to address.

One aspect of increased molten glass flow rate is the increased heat load imposed on the manufacturing apparatus, which can upset the thermal balance of the process, from melting furnace to below the forming body. That is, as the flow rate increases, methods must be found to adequately cool the molten glass to achieve the appropriate molten glass viscosity and forming characteristics, particularly within the draw portion of the process.

To maintain a reasonably consistent environment, both the forming body and the free space region through which the molten glass ribbon is drawn as it transitions from a viscous liquid to an elastic solid is contained within structures that separate the molten glass ribbon from the surrounding environment. More particularly, the free space volume through which the glass ribbon is drawn is surrounded on at least four sides by a housing positioned below the forming body: a collection of connected walls and refractory insulation that form a shroud or open-ended box, or, in effect, a vertically oriented tunnel. Heating and/or cooling devices (not shown) necessary to control the temperature of the ribbon (e.g., cool the ribbon) are positioned within the housing along draw direction 60 and in a width (lateral) direction orthogonal to the draw direction. Such heating and cooling devices can comprise electrical heating elements, cooling coils through which a coolant is flowed, or other devices, such as lasers configured to control the temperature of the ribbon. Such devices are well known to those of skill in the art and are not further described here.

As noted, it is particularly beneficial during the drawing process to maintain a well-controlled temperature regime at the temperature range over which the viscous ribbon transitions to an elastic solid. Moreover, it is desirable to cool the molten glass ribbon as quickly as possible after the molten glass leaves the forming body to maximize the available space needed to anneal the glass ribbon. Increasing the anneal period allows time for the glass to undergo additional relaxation.

Relaxation behavior is important for many glass products. For example, liquid crystal display glass is subjected to thermal treatments during deposition of thin film transistors on the glass substrate. Relaxation of the glass during these heat treatment cycles can lead to compaction, i.e., a permanent change in the dimensions of the glass brought about by a densification of the glass. The quality of glass for precision products, such as LCD manufacture, depends on obtaining a uniform thermal history throughout the glass; any uneven relaxation effect will lead to a deterioration of the quality of the final product through optical inhomogeneity (e.g., birefringence). When glass sheets are used as substrates and subjected to elevated temperature during processing, glass relaxation can cause dimensional changes that impact subsequent manufacturing processes. Minimal dimensional change during customer processes can be a key attribute of the glass. Thus, the ability to accurately predict compaction under a specific set of process conditions would be beneficial.

There are two important factors governing glass relaxation: thermodynamics and kinetics. Thermodynamically, glass is a non-equilibrium system that wants to relax. While the presence of a thermodynamic driving force is a necessary condition for glass relaxation, it is by itself insufficient. The glass must also have sufficient thermal energy and time to enable the kinetics of relaxation. Assuming isobaric conditions, the kinetics of the glass depend on three factors: composition, temperature, and thermal history. The importance of thermal history cannot be overstated, since the dynamic behavior of two glasses of the same composition and at the same temperature can vary by many orders of magnitude depending on the details of their thermal history.

The production of liquid crystal displays, for example active matrix liquid crystal display devices (AMLCDs), is complex, and the properties of the substrate glass are extremely important. First and foremost, the glass substrates used in the production of liquid crystal display devices need to have their physical dimensions tightly controlled.

In the liquid crystal display field, thin film transistors (TFTs) based on poly-crystalline silicon are preferred for their ability to transport electrons more effectively. Poly-crystalline based silicon transistors ($\rho$-Si) are characterized as having a higher mobility than those based on amorphous-silicon based transistors ($\alpha$-Si). This allows the manufacture of smaller and faster transistors, which ultimately produces brighter and faster displays. One problem with $\rho$-Si based transistors is that their manufacture requires higher process temperatures than those employed in the manufacture of $\alpha$-Si transistors. Process temperatures can range from about 450° C. to about 700° C. compared to peak temperatures of about 350° C. typically employed in the manufacture of $\alpha$-Si transistors. At temperatures suitable for $\rho$-Si deposition, most AMLLCD glass substrates undergo compaction. Compaction, also referred to as thermal stability or dimensional change, is an irreversible dimensional change (shrinkage) in the glass substrate due to changes in the fictive temperature of the glass. "Fictive temperature" is a concept used to indicate the structural state of a glass. Glass that is cooled quickly from a high temperature typically exhibits a higher fictive temperature than an identical glass cooled from the same temperature more slowly because of the "frozen in" higher temperature structure. When a glass is held at an elevated temperature, the glass structure is allowed more time to relax toward the heat treatment temperature structure. Since the fictive temperature of the glass substrate used in LCD construction is almost always above the relevant heat treatment temperatures encountered during thin film transistor (TFT) processes, structural relaxation that occurs as a result of the high temperature heat treatment causes a decrease in fictive temperature that causes an increase in the glass density and a commensurate shrinkage (compaction).

It would be advantageous to minimize the propensity of the glass to compact because compaction can create possible alignment issues during the display manufacturing process (e.g., during transistor deposition), which in turn may create performance issues in the finished display.

There are several approaches to minimize compaction in glass. One approach is to thermally pretreat the glass to create a fictive temperature similar to the temperature the glass will experience during $\rho$-Si TFT manufacture. There are several difficulties with this approach. First, the multiple heating steps employed during the $\rho$-Si TFT manufacture create slightly different fictive temperatures in the glass that cannot be fully compensated for by pretreatment. Second, the thermal stability of the glass becomes closely linked to the details of the particular $\rho$-Si TFT manufacture, which can mean different pretreatments for different end-users. Finally, pretreatment adds to process cost and complexity.

Another approach involves slowing the cooling rate during manufacture. While such an approach has merits, some manufacturing techniques, such as the fusion process, have only limited space available during the drawing process to perform the slow cooling. Consequently, relatively rapid quenching of the glass ribbon occurs, and a relatively high temperature structure (high fictive temperature) is "frozen in". While controlling the cooling rate(s) is possible with such a manufacturing process, development of optimal cooling rates that minimize compaction can be difficult.

Historically, cooling rates for a given glass have been "borrowed" from similar glasses manufactured under similar process conditions. That is, a cooling curve applied to one glass composition under one set of process conditions may be applied to the manufacturing, for example, of a another glass that is of a similar composition to the first glass as a starting point. Similarly, changes to process conditions, such as an increase in throughput (e.g., glass flow rate), begins with the lower-flow cooling rates. In either case, optimization of this initial cooling curve, for example to minimize compaction for the new glass and/or process conditions, is undertaken on a "best guess" basis, wherein changes are made to the individual cooling rates comprising the initial cooling curve using experience and, to a large degree, luck. The resultant glass is tested, and if the attribute of choice, such as compaction, is unsatisfactory, the cooling rates are modified. The process is an iterative process played out in real time by the actual drawing and testing of glass. It can be a lengthy endeavor and yet may not result in the best cooling curve to deliver optimal compaction performance.

It was long thought that the most beneficial cooling curve in the context of compaction comprised a fast cooling rate during the time the glass was in a generally low viscosity state (e.g., less than about $10^{10}$ poise), after which the glass was cooled at a significantly slower rate in a viscosity region at or about the anneal point of the glass (the anneal point is defined as the temperature at which glass viscosity is equal to $10^{13.18}$ Poise). For example, U.S. Pat. No. 8,136,371 describes a cooling regime where slow cooling is performed between the anneal point and 50° C. less than the anneal point. As discussed herein below, the present inventors have discovered that the sensitivity of compaction to cooling rate can, unexpectedly, extend to temperatures well below the anneal point. Thus, simply adjusting historical cooling rates with minimal guidance may not place the slow cooling regime in the appropriate temperature range to minimize compaction. It would be beneficial to be able to predict compaction for a given set of process conditions and/or glass compositions to both ensure a maximum reduction in compaction and to reduce time spent searching for the appropriate cooling curve by trial and error.

Accordingly, a partial empirical method capable of predicting compaction is disclosed. In a first step, data from a plurality of process conditions is obtained. This data may be obtained from operational draws during normal, stable manufacturing, or from laboratory experiments. The data may include, for example, temperature of the glass ribbon along a centerline of the glass ribbon as a function of time and/or distance from the root of the forming body (since both are directly relatable), cooling rate (obtainable from the temperature, and time and/or distance from the root), and measured compaction for at least one glass sheet cut from each glass ribbon. Cooling rates can be calculated, for example, at a predetermined distance or temperature interval, for instance at every 10° C., every 15° C., or any other suitable interval that provides the desired measurement resolution. It should be evident in view of the foregoing that the temperature of the glass ribbon changes as a function of distance from the forming body root, which has an equivalency in time, and therefore the interval can be selected based on time, location (distance) or temperature. In most scenarios, it may be acceptable to eliminate cooling rates at temperatures below about 450° C. and above about 900° C., since at glass temperatures below 450° C. and above 900° C. compaction can be assumed to not be affected by cooling rate. That is, at temperatures above about 900° C., relaxation of the ribbon can be assumed to be sufficiently rapid that compaction is of little concern, and at temperatures below about 450° C., the glass ribbon is sufficiently cooled that compaction behavior is frozen in and therefore unaffected by thermal treatment at such low temperatures. If desired, multiple glass sheets may be measured for compaction for each process condition to improve confidence in the data. The data may be obtained from multiple draw apparatus or draw conditions for a given glass composition.

Once the foregoing data has been collected and/or calculated, a system of simple linear regression equations can be employed with cooling rates as predictor variables and compaction as response variables, as shown in equation (1) below, $$\begin{bmatrix} k \\ \vdots \\ k \end{bmatrix} + \begin{bmatrix} q_1^1 & \cdots & q_1^n \\ \vdots & \ddots & \vdots \\ q_i^1 & \cdots & q_i^n \end{bmatrix} \times \begin{bmatrix} b_1 \\ \vdots \\ b_n \end{bmatrix} = \begin{bmatrix} C_1 \\ \vdots \\ C_i \end{bmatrix}, \quad (1)$$

where q represents cooling rate in ° C./second, b represents the regression coefficients, C represents compaction in parts per million (ppm), i represents the number of data sets (number of unique sets of process conditions), n represents the number of regression coefficients, and k represents the regression intercept.

Since the number of data sets may not equal the number of regression coefficients, principal component regression techniques may be used to find an appropriate set of coefficients. Alternatively, the coefficient calculation can be regularized by defining a penalty parameter that penalizes the differences among coefficients. Such techniques are well known and not further described herein.

Once the regression coefficients have been calculated, for a given target cooling curve cooling rates within a predetermined temperature range from x° C. to y° C. can be obtained and a compaction value calculated using the regression coefficients in accordance with equation (2), $$\text{Compaction} = k + \Sigma_{n=1}^{n=m}(b_n \times q_n), \quad (2)$$

where the summation is carried out over the predetermined range from x to y. In some embodiments, the summation may extend over a finite temperature range, for example over a range from 450° C. to 900° C., however, a range from 450° C. to 900° C. is provided as an example only, and other temperature ranges may be employed as desired. For example, in embodiments, x can be equal to or greater than 450° C. and y can be equal to or less than 950° C.

Minimizing compaction then becomes an iterative calculation process, involving modification of the initial cooling curve and subsequent calculation of a predicted compaction of the new, modified cooling curve, and may be driven, in part, by knowledge obtained by examining the regression coefficients. This is illustrated by the following example.

Figure 3:
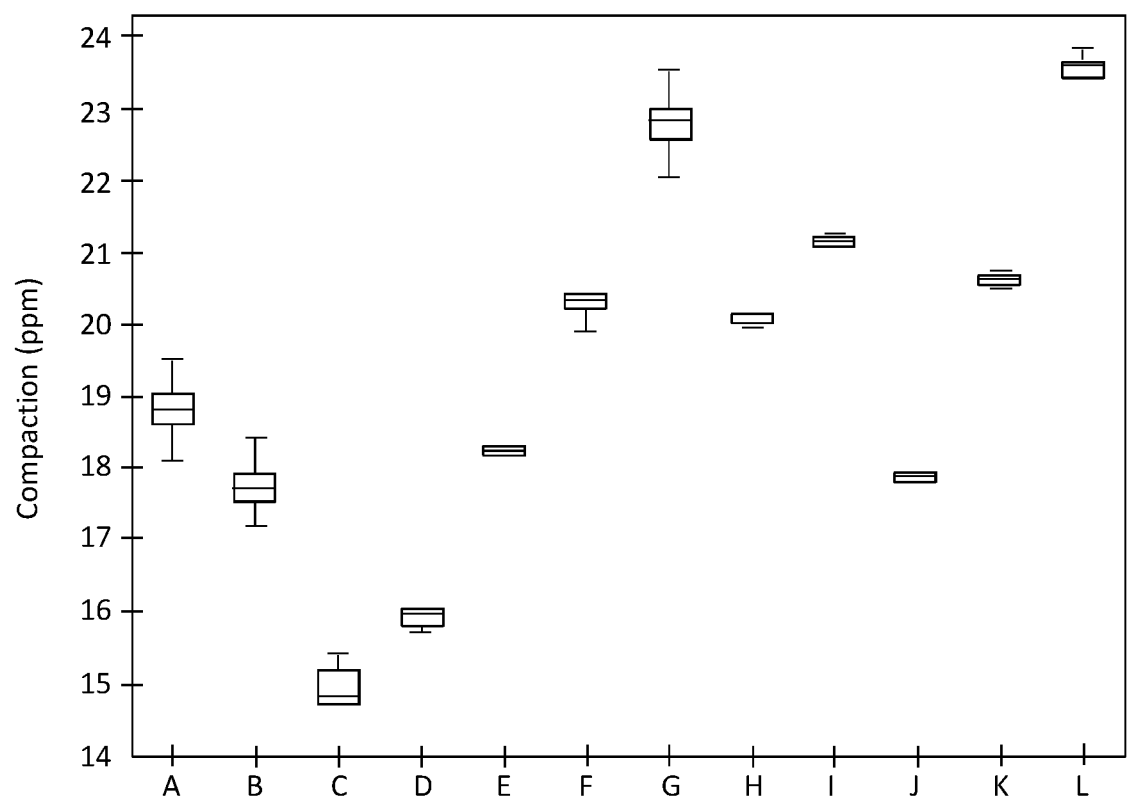
FIG. 3 is a plot of compaction as a function of various sets of draw conditions labeled as A through L.

Corning® Lotus™ glass was drawn as glass ribbons from different draw apparatus under different process conditions, including different thicknesses, flow rates and cooling rates, and compaction values were measured for glass sheets cut from the various ribbons. In all, data for 12 different process conditions was collected. Compaction for glass ribbons from each set of process conditions was measured by placing a glass sheet cut from each ribbon on a table with fiducial markings thereon, fixing the glass sheet such that the glass sheet could be removed and then accurately replaced. Matching fiducial markings were marked on the glass sheet. The glass sheet was removed and heated in an oven to a temperature of 590° C., and held at that temperature for a total of 30 minutes. After cooling the glass sheet at the oven rate (natural rate of cooling with the oven power off) to room temperature, the glass sheet was replaced on the table in the original position, and the distance between the fiducial markings on the glass sheet and the fiducial markings on the table were measured. The distance between the two sets of fiducial markings represented a compaction value expressed in ppm. Glass sheets for each process condition were measured for compaction multiple times and averaged. Compaction for all 12 sets of process conditions is plotted in FIG. 3. The data show a significant spread in compaction values, with glass sheet formed at a thickness of 0.7 mm thickness (Sample C) exhibiting the least compaction, and glass sheet formed with a thickness of 0.3 mm (Samples G and L) exhibiting the greatest compaction.

Figure 4:
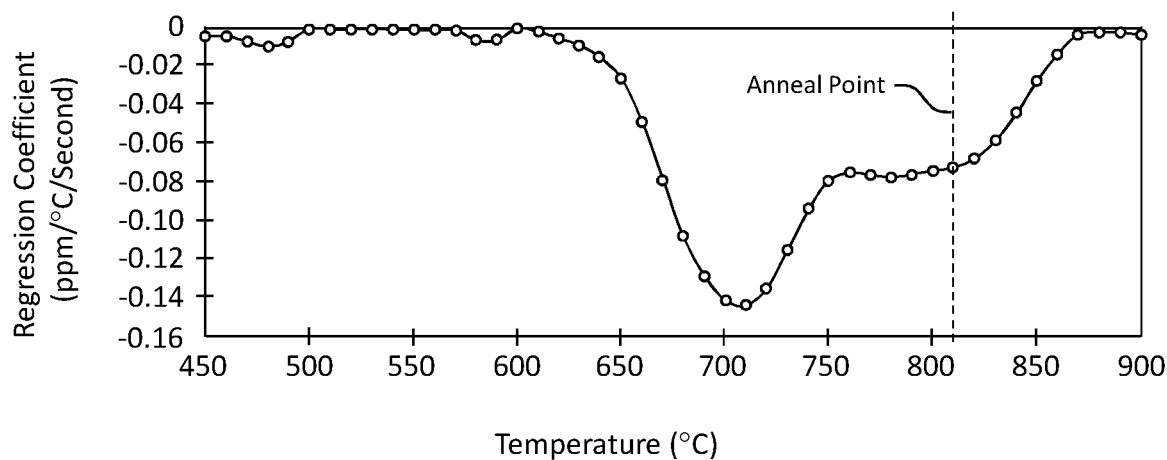
FIG. 4 is a plot of regression coefficients obtained by correlating the draw conditions and compaction of FIG. 3.

The process data and compaction values for the foregoing samples was set to the form of equation (1), with n=46 (46 regression coefficients) and i=12 (12 data sets), and solved for the regression coefficients b. The number of regression coefficients will vary depending on the selected temperature interval at which the cooling rate data is calculated. In this example, data was collected at intervals of 10° C. in a range from 450° C. to 950° C., although other intervals and ranges can be used, depending on need and the resolution desired. A plot of the regression coefficients as a function of temperature is provided in FIG. 4. Larger negative numbers represent greater impact on compaction. For reference, the anneal point of Corning Lotus glass is 810° C. Examination of FIG. 4 reveals that cooling rates for this particular glass in a range from about 660° C. to about 850° C. are the most impactful relative to compaction. More importantly, the greatest impact on compaction occurs at a temperature of about 710° C., fully 100° C. less than the anneal point. It should be emphasized that these results pertain to the tested glass and that specific values may differ for other glass compositions. However, it remains that an examination of the regression coefficients provides insight into compaction behavior useful for guiding modification of a cooling curve, and that compaction can be meaningfully impacted at temperatures well below the anneal point.

Figure 5:
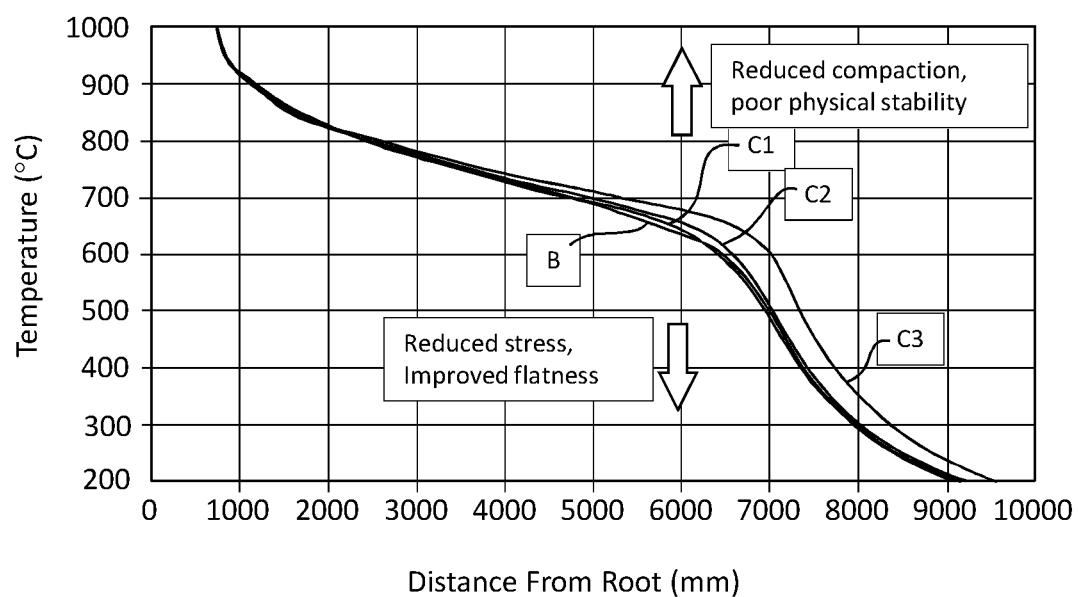
FIG. 5 is a plot graphically illustrating several target cooling curves (temperature as a function of distance from the forming body) produced using the regression coefficients of FIG. 4.

FIG. 5 depicts four cooling curves related to the foregoing example. Curve B represents a baseline (historical cooling curve), whereas curves C1 through C3 represent three target cooling curves obtained by varying the cooling rates of the baseline cooling curve. Glass was drawn in a fusion down draw process using the four cooling curves. Additionally, compaction was both predicted using equation (2) and measured.

Figure 6:
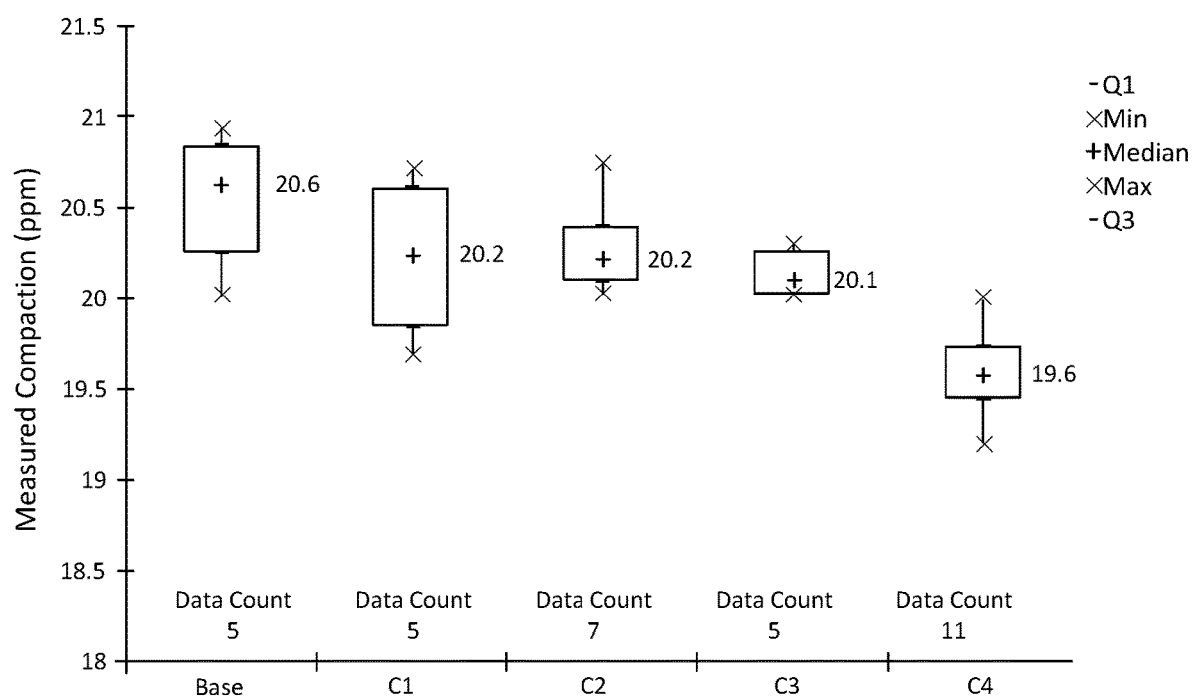
FIG. 6 is a plot of measured compaction obtained from the cooling curves of FIG. 5.

Examination of curves C1-C3 reveal that while cooling curves C1 and C2 closely follow the behavior of baseline curve B, cooling curve C3 exhibits a greater slowing of the cooling rate in the region of about 700° C. (commensurate with the indications of FIG. 4), and which comparatively slower cooling rate extends for a greater distance relative to the root of the forming body than the other cooling curves. FIG. 6 graphically depicts (via box plots) measured compaction values for each of the cooling curves of FIG. 5, and indicates the number of measured samples for each cooling curve. Compaction for each cooling curve was also predicted using equation (2). The results are presented in Table 1 below, where the predicted (modeled) compaction values and the measured compaction values are provided in units of ppm.

TABLE 1

| Condition | Model Results | Measured |
|---|---|---|
| Base | 20.60 | 20.6 |
| C1 | 20.24 | 20.2 |
| C2 | 20.10 | 20.3 |
| C3 | 19.77 | 19.6 |

Table 1 shows excellent agreement between the modeled (predicted) compaction values. The data also show the cooling curve C3 results in a full 1 ppm improvement in measured compaction values compared to results from the baseline cooling curve.

Referring back to FIG. 5, it should be further noted that the target cooling curves C1-C3 may also take into account considerations other than compaction. For example, adjusting a cooling curve for compaction may affect other attributes of the glass ribbon, such as flatness of the ribbon. Thus, while it is desirable to reduce compaction, compaction should not be reduced such that other attributes suffer. As FIG. 5 depicts, movement of the cooling curves upward (tilting upward), has the intended effect of reducing compaction, but may affect the physical stability of the ribbon as the glass ribbon is drawn from the forming body. Alternatively, tilting the cooling curves downward has the effect of reducing stress in the ribbon and therefore improving flatness, but at the expense of increased compaction. Accordingly, the improvement in compaction should be weighed against any detrimental effects on other ribbon attributes, such as residual stress and ribbon shape.

Thermal strain in the glass ribbon in a fusion forming process determines stress and shape in both the ribbon and in glass sheets cut from the ribbon, and can be calculated from a viscoelastic model. Such models can be used to develop a metric useful for evaluating stress in the glass ribbon. Ideally, thermal stress in the glass ribbon should be zero, or a tensile stress, so that the glass ribbon exhibits substantially zero warping. However, such treatment of stress cannot be applied universally across the entire width of the glass ribbon. For example, the glass ribbon typically comprises thickened lateral edge portions, termed "beads", owing largely to surface tension effects during the draw process. Consequently, stress resulting from the beads can be individually modeled. A separate metric can be developed for the effect of the bead on shape of the glass ribbon. Broadly then, a more complete development of a cooling curve taking into account other variables and considerations can include development of both a glass viscoelastic material model and a parameterized thermal model for ribbon temperature. Weights can be assigned to the various components of the objective (for example compaction) to be optimized, and an optimal temperature field for the ribbon can be calculated by manipulating the parameters of the thermal model until the objective is minimized. Application of the calculated temperature field to an actual process is done by manipulating heater power, air flow, water cooling, etc.

It will be apparent to those skilled in the art that various modifications and variations can be made to embodiments of the present disclosure without departing from the spirit and scope of the disclosure. Thus it is intended that the present disclosure cover such modifications and variations provided they come within the scope of the appended claims and their equivalents.

What is claimed is:
1. A method of controlling compaction, comprising:
   a) measuring compaction values for a plurality of glass sheets cut from a plurality of glass ribbons, the glass ribbons formed with different cooling rates at temperature increments of at least 10° C. in a temperature range equal to or greater than 450° C. and equal to or less than 900° C.;
   b) correlating the measured compaction values with the cooling rates of step a) to obtain a plurality of regression coefficients corresponding to a plurality of temperatures, wherein step b) comprises a linear regression, wherein the linear regression comprises a system of linear equations of the form

$$\begin{bmatrix} k \\ \vdots \\ k \end{bmatrix} + \begin{bmatrix} q_1^1 & \cdots & q_1^n \\ \vdots & \ddots & \vdots \\ q_i^1 & \cdots & q_i^n \end{bmatrix} \times \begin{bmatrix} b_1 \\ \vdots \\ b_n \end{bmatrix} = \begin{bmatrix} C_1 \\ \vdots \\ C_i \end{bmatrix},$$

where q represents cooling rate in ° C./second, b represents regression coefficients, C represents compaction in parts per million, i represents a total number of data sets, n represents a total number of the regression coefficients, and k represents an intercept of the regression;
   c) selecting a predetermined cooling curve, the predetermined cooling curve comprising a plurality of predetermined cooling rates at the corresponding plurality of temperatures of step b);
   d) using the plurality of regression coefficients and the plurality of predetermined cooling rates to calculate a predicted compaction value, wherein the predicted compaction value is equal to $$\text{Compaction} = k + \sum_{n=1}^{n=m} (b_n \times q_n),$$

where m represents a number of the temperature increments over a temperature range from 450° C. to 900° C.;
   e) modifying the predetermined cooling rates to minimize the predicted compaction value and obtain target cooling rates;
   f) drawing a subsequent glass ribbon using the target cooling rates.

2. The method according to claim 1, further comprising substituting the modified cooling rates for the predetermined cooling rates and repeating steps d) and e).

3. A method of controlling compaction, comprising:
   a) drawing a glass ribbon from a forming body at a first draw rate;
   b) measuring temperature along a centerline of the glass ribbon at a plurality of distances from a bottom edge of the forming body;
   c) calculating cooling rates for the glass ribbon at the plurality of distances based on the measured temperatures;
   d) measuring a compaction value of a glass sheet cut from the glass ribbon;

e) repeating steps a) through d) for a plurality of glass ribbons drawn at a plurality of draw rates to obtain a plurality of measured compaction values;

f) correlating the plurality of measured compaction values with the cooling rates at the plurality of distances for the plurality of glass ribbons to obtain a plurality of regression coefficients corresponding to a plurality of temperatures, wherein step f) comprises a linear regression, wherein the linear regression comprises a system of linear equations of the form $$\begin{bmatrix} k \\ \vdots \\ k \end{bmatrix} + \begin{bmatrix} q_1^1 & \cdots & q_1^n \\ \vdots & \ddots & \vdots \\ q_i^1 & \cdots & q_i^n \end{bmatrix} \times \begin{bmatrix} b_1 \\ \vdots \\ b_n \end{bmatrix} = \begin{bmatrix} C_1 \\ \vdots \\ C_i \end{bmatrix},$$

where q represents cooling rate in °C./second, b represents regression coefficients, C represents compaction in parts per million, i represents a total number of data sets, n represents a total number of the regression coefficients, and k represents an intercept of the regression;

g) selecting a predetermined cooling curve, the predetermined cooling curve comprising a predetermined cooling rate at each corresponding temperature of the plurality of temperatures;

h) using the plurality of regression coefficients and the plurality of predetermined cooling rates to obtain a predicted compaction value at a predetermined draw rate, wherein the predicted compaction value is equal to $$\text{Compaction} = k + \sum_{n=1}^{n=m} (b_n \times q_n),$$

where m represents a number of the temperature increments over a temperature range from 450° C. to 900° C.;

i) modifying the predetermined cooling rates to minimize the predicted compaction value at the predetermined draw rate and obtain target cooling rates;

j) drawing a subsequent glass ribbon using the target cooling rates.

4. The method according to claim 3, further comprising substituting the modified cooling rates of step i) for the predetermined cooling rates of step h), and repeating steps h) and i) to obtain new target cooling rates prior to step j).

* * * * *